US010023551B2

(12) United States Patent
Brown et al.

(10) Patent No.: US 10,023,551 B2
(45) Date of Patent: Jul. 17, 2018

(54) GLUTATHIONE-CLEAVABLE PRODRUG AND METHODS OF USE THEREOF

(71) Applicant: GEORGETOWN UNIVERSITY, Washington, DC (US)

(72) Inventors: Milton L. Brown, Brookeville, MD (US); Yali Kong, Fairfax, VA (US); Jacqueline Smith, Bowie, MD (US); Kan Wang, Gaithersburg, MD (US); Shujie Hou, Gaithersburg, MD (US)

(73) Assignee: Georgetown University, Washington, DC (US)

( * ) Notice: Subject to any disclaimer, the term of this patent is extended or adjusted under 35 U.S.C. 154(b) by 0 days.

(21) Appl. No.: 15/573,183

(22) PCT Filed: May 12, 2016

(86) PCT No.: PCT/US2016/032088
§ 371 (c)(1),
(2) Date: Nov. 10, 2017

(87) PCT Pub. No.: WO2016/183315
PCT Pub. Date: Nov. 17, 2016

(65) Prior Publication Data
US 2018/0105505 A1    Apr. 19, 2018

Related U.S. Application Data

(60) Provisional application No. 62/160,385, filed on May 12, 2015.

(51) Int. Cl.
| | |
|---|---|
| *C07D 311/58* | (2006.01) |
| *C07D 311/02* | (2006.01) |
| *A61P 35/00* | (2006.01) |
| *G01N 21/64* | (2006.01) |
| *A61K 47/69* | (2017.01) |
| *C07C 321/14* | (2006.01) |
| *C07C 69/017* | (2006.01) |
| *C07C 69/003* | (2006.01) |
| *C07C 271/28* | (2006.01) |

(52) U.S. Cl.
CPC ........ *C07D 311/02* (2013.01); *A61K 47/6957* (2017.08); *A61P 35/00* (2018.01); *C07C 69/003* (2013.01); *C07C 69/017* (2013.01); *C07C 271/28* (2013.01); *C07C 321/14* (2013.01); *C07D 311/58* (2013.01); *G01N 21/64* (2013.01)

(58) Field of Classification Search
CPC .................................................. C07D 311/58
See application file for complete search history.

(56) References Cited

FOREIGN PATENT DOCUMENTS

| CN | 104208724 | 12/2014 |
| CN | 104945409 A | 9/2015 |

OTHER PUBLICATIONS

Balendiran, et al., "The role of glutathione in cancer", Cell Biochem Funct 2004, vol. 22 (6), pp. 343-352.
Barbon, et al., "Triplet states of the nonlinear optical chromophore DCM in single crystals of potassium hydrogen phthalate and their relationship to single-molecule dark states", J. Am. Chem. Soc. 2009, vol. 131 (32), pp. 11548-11557.
Cacciatore, et al., "Prodrug approach for increasing cellular glutathione levels", Molecules 2010, vol. 15 (3), pp. 1242-1264.
Chinigo, et al., "Asymmetric synthesis of 2,3-dihydro-2-arylquinazolin-4-ones: methodology and application to a potent fluorescent tubulin inhibitor with anticancer activity", J Med Chem. Aug. 14, 2008, vol. 51(15) pp. 4620-4631. doi: 10.1021/jm800271c. Epub Jul. 9, 2008. PMID:18610995.
Frangioni, "In vivo near-infrared fluorescence imaging", Curr. Opin. Chem. Biol. 2003, vol. 7 (5), pp. 626-634.
Guo, et al., "Dicyanomethylene-4H-pyran chromophores for OLED emitters, logic gates and optical chemosensors", Chem. Commun. 2012, vol. 48 (49), pp. 6073-6084.
Guo, et al., "Intramolecular charge-transfer process based on dicyanomethylene-4H-pyran derivative: An integrated operation of half-subtractor and comparator", J. Phys. Chem. C 2008, vol. 112 (17), pp. 7047-7053.
Guo, et al., "Hydrophilic Copolymer Bearing Dicyanomethylene-4H-pyran Moiety As Fluorescent Film Sensor for Cu2+ and Pyrophosphate Anion", Macromolecules 2010, vol. 43 (2), pp. 739-744.
Higgins, et al., "Targeted therapies for breast cancer", J. Clin. Invest. 2011, vol. 121 (10), pp. 3797-3803.
Huang, et al., "A colorimetric and fluorescent turn-on sensor for pyrophosphate anion based on a dicyanomethylene-4H-chromene framework", Chem. Commun. 2008, Vol (41), pp. 5143-5145.
Iyer, et al., "Induction of apoptosis in proliferating human endothelial cells by the tumor-specific antiangiogenesis agent combretastatin A-4", Cancer Res 1998, vol. 58 (20), pp. 4510-4514.
Kerksick, et al., "The antioxidant role of glutathione and N-acetyl-cysteine supplements and exercise-induced oxidative stress", J. Int. Soc. Sports Nutr., 2005, vol. 2, pp. 38-44.
Kong, et al., "Structure-based discovery of a boronic acid bioisostere of combretastatin A-4", Chem. Biol. 2005, vol. 12 (9), pp. 1007-1014.
Kong, et al., "A boronic acid chalcone analog of combretastatin A-4 as a potent anti-proliferation agent", Bioorg Med Chem. Jan. 15, 2010; vol. 18(2) pp. 971-977. doi: 10.1016/j.bmc.2009.11.003. Epub Nov. 10, 2009. PMID: 20006519.
Lee, et al., "Design, synthesis, and biological evaluations of 2,5-diaryl-2,3-dihydro-1,3,4-oxadiazoline analogs of combretastatin-A4", J. Med. Chem. 2010, vol. 53 (1), pp. 325-334.

(Continued)

*Primary Examiner* — Laura L. Stockton
(74) *Attorney, Agent, or Firm* — Kilpatrick Townsend & Stockton, LLP

(57) ABSTRACT

A glutathione-cleavable prodrug is provided herein, as well as methods for its use in treating cancer, including triple negative breast cancer. The prodrug can be cleaved by glutathione under physiological conditions to generate a biologically active agent. The compound described herein is advantageous as the compound is fluorescent and can therefore be monitored within a subject.

22 Claims, 15 Drawing Sheets

(56) References Cited

OTHER PUBLICATIONS

Liou, et al., "Concise synthesis and structure-activity relationships of combretastatin A-4 analogues, 1-aroylindoles and 3-aroylindoles, as novel classes of potent antitubulin agents", J. Med. Chem. 2004, vol. 47 (17), pp. 4247-4257.

Liu, et al., "Conveniently synthesized isophorone dyes for high efficiency dye-sensitized solar cells: tuning photovoltaic performance by structural modification of donor group in donor-pi-acceptor system", Chem. Commun. 2009, vol. (13), pp. 1766-1768.

Lu, et al., "Design, synthesis, and biological evaluation of stable colchicine binding site tubulin inhibitors as potential anticancer agents", J. Med. Chem. 2014, vol. 57 (17), 7355-66.

Luo, et al., "A review of NIR dyes in cancer targeting and imaging", Biomaterials, 2011, vol. 32 (29), pp. 7127-7138.

Meyer, et al., "A phase I trial of radioimmunotherapy with 131I-A5B7 anti-CEA antibody in combination with combretastatin-A4-phosphate in advanced gastrointestinal carcinomas", Clin. Cancer Res. 2009, vol. 15 (13), pp. 4484-4492.

Mooberry, et al., "Identification and characterization of a new tubulin-binding tetrasubstituted brominated pyrrole" Mol Pharmacol. Jul. 2007, vol. 72(1) pp. 132-140. Epub Apr. 24, 2007. PMID: 17456786.

Morales, et al., "Intracellular glutathione levels determine cell sensitivity to apoptosis induced by the antineoplasic agent N-(4-hydroxyphenyl) retinamide", Anticancer Res, 2005, vol. 25 (3B), pp. 1945-1951.

Nathan, et al., "Phase I trial of combretastatin A4 phosphate (CA4P) in combination with bevacizumab in patients with advanced cancer", Clin. Cancer Res. 2012, vol. 18 (12), pp. 3428-3439.

PCT/US2016/032088, "International Preliminary Report on Patentability", dated Nov. 23, 2017, 5 pages.

PCT/US2016/032088, "International Search Report and Written Opinion", dated Jul. 7, 2016, 6 pages.

Pettit, et al., "Antineoplastic agents. 487. Synthesis and biological evaluation of the antineoplastic agent 3,4-methylenedioxy-5,4'-dimethoxy-3'-amino-Z-stilbene and derived amino acid amides", J. Med. Chem. 2003, vol. 46 (4), pp. 525-531.

Ramsay, et al., "Glutathione S-conjugates as prodrugs to target drug-resistant tumors", Front. Pharmacol. 2014, vol. 5, Article 181, pp. 1-16.

Rodriguez-Ramos, et al., "Synthesis, docking study and relaxant effect of 2-alkyl and 2-naphthylchromones on rat aorta and guinea-pig trachea through phosphodiesterase inhibition", Bioorg Chem, 2013, vol. 50, pp. 17-25.

Ruzza, et al., "Glutathione Transferase (GST)-Activated Prodrugs", Pharmaceutics 2013, vol. 5 (2), pp. 220-231.

Siemann, et al., "A review and update of the current status of the vasculature-disabling agent combretastatin-A4 phosphate (CA4P)", Expert Opin. Investig. Drugs 2009, vol. 18 (2), pp. 189-197.

Sun, et al., "A two-photon fluorescent probe with near-infrared emission for hydrogen sulfide imaging in biosystems", Chem Commun (Camb), 2013, vol. 49 (37), pp. 3890-3892.

Tong, et al., "Color-tunable, aggregation-induced emission of a butterfly-shaped molecule comprising a pyran skeleton and two cholesteryl wings", J. Phys. Chem. B 2007, vol. 111 (8), pp. 2000-2007.

Tron, et al., "Medicinal chemistry of combretastatin A4: present and future directions" J. Med. Chem. 2006, vol. 49 (11), pp. 3033-3044.

Wu, et al., "In Vivo and in Situ Tracking Cancer Chemotherapy by Highly Photostable NIR Fluorescent Theranostic Prodrug", JACS, 2014, vol. 136, No. 9, pp. 3579-3588.

Yang, et al., "Luminescent chemodosimeters for bioimaging", Chem. Rev. 2013, vol. 113 (1), pp. 192-270.

Young, et al., "Combretastatin A4 phosphate: background and current clinical status", Expert Opin. Investig. Drugs 2004, vol. 13 (9), pp. 1171-1182.

Zhao, et al., "A controlled-release nanocarrier with extracellular pH value driven tumor targeting and translocation for drug delivery" Angew. Chem., Int. Ed. Engl 2013, vol. 52 (29), pp. 7487-7491.

Zhu, et al., "A novel NIR fluorescent turn-on sensor for the detection of pyrophosphate anion in complete water system", Chem. Commun. 2012, vol. 48 (12), pp. 1784-1786.

Zweifel, et al., "Phase II trial of combretastatin A4 phosphate, carboplatin, and paclitaxel in patients with platinum-resistant ovarian cancer", Ann. Oncol. 2011, vol. 22 (9), pp. 2036-2041.

GLUTATHIONE-CLEAVABLE PRODRUG AND METHODS OF USE THEREOF

CROSS REFERENCE TO RELATED APPLICATION

This application claims priority to U.S. Provisional Application No. 62/160,385, filed May 12, 2015, which is incorporated herein by reference in its entirety.

BACKGROUND

The effectiveness of chemotherapy for anticancer treatment purposes has been largely restricted by its harmful side effects caused by a lack of selectivity and difficulty in treatment monitoring. One of the most promising enhancements of cancer treatment is the development of selective drug delivery mechanisms that are capable of releasing treatments in response to individual tumor microenvironments. A promising potential mechanism for specific drug delivery is glutathione (GSH)-mediated prodrug activation. In normal cells, glutathione is an important antioxidant that prevents oxidative stress to various parts of the cell. Cancer cells have a 30-40 times greater glutathione concentration than healthy cells. Various prodrug systems have been developed that release treatment drugs in response to glutathione. However, few mechanisms have been developed that can effectively monitor the release of such treatments after stimulation by GSH.

Theranostic prodrugs, equipped with both fluorophoric biomarkers and small molecule drugs, are designed to improve drug delivery monitoring due to their ability to concurrently release their biomarker and drug constituents. However, most of the fluorophores used as theranostic prodrugs suffer from short wavelength emission, tissue autofluorescence interference, and photoinstabilities.

SUMMARY

Described herein is a glutathione-cleavable prodrug, which is a near-infrared, fluorescent theranostic compound. Near-infrared (NIR) fluorophores, as the signaling unit in prodrugs, can penetrate tissue deeply with little damage, and the NIR wavelength range of 700-1000 nm escapes the range of tissue autofluorescence, allowing for greater accuracy in detection. The glutathione-cleavable prodrug as described herein includes the following compound:

Also described herein are compositions comprising a compound as described herein and a pharmaceutically acceptable carrier. Additionally described herein are kits comprising a compound or composition as described herein.

Further described herein are methods of treating or preventing cancer in a subject, comprising administering to the subject an effective amount of a compound or composition as described herein. Optionally, the cancer is breast cancer (e.g., triple negative breast cancer).

Also described herein are methods of inhibiting angiogenesis in a subject. The methods of inhibiting angiogenesis in a subject comprise administering to the subject an effective amount of a compound or composition as described herein. Optionally, the subject has cancer (e.g., triple negative breast cancer). Optionally, the cancer overexpresses glutathione.

Also described herein are methods of inhibiting tubulin polymerization in a cell. The methods of inhibiting tubulin polymerization in a cell comprise contacting the cell with an effective amount of a compound or composition as described herein. Optionally, the cell is a cancer cell (e.g., a triple negative breast cancer cell). Optionally, the cell is a cell that overexpresses glutathione. The contacting in the methods described herein can be performed in vivo or in vitro.

Methods of delivering combretastatin A-4 to a cell through use of a combretastatin A-4 prodrug are further described herein. The method comprises contacting a cell comprising glutathione with a compound as described herein. In this method, the glutathione cleaves the compound to form combretastatin A-4. Optionally, the cell is a cancer cell (e.g., a triple negative breast cancer cell). Optionally, the cell is a cell that overexpresses glutathione. The contacting in the methods described herein can be performed in vivo or in vitro.

Methods of imaging a glutathione containing cell or population of cells in a subject are also provided herein. The methods of imaging a glutathione containing cell or population of cells in a subject comprises administering to the subject a compound as described herein and detecting fluorescence in the subject, wherein fluorescence indicates a glutathione containing cell or population of cells.

The details of one or more embodiments are set forth in the drawings and the description below. Other features, objects, and advantages will be apparent from the description and drawings, and from the claims.

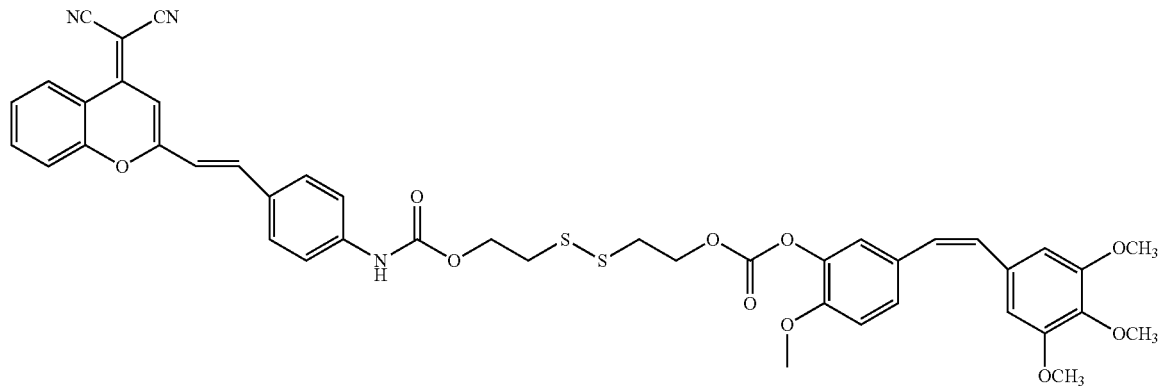 [SMILES: COc1ccc(/C=C\c2cc(OC)c(OC)c(OC)c2)cc1OC(=O)OCCSSCCOC(=O)Nc1ccc(/C=C/C2=CC(=C(C#N)C#N)c3ccccc3O2)cc1]

or a pharmaceutically acceptable salt thereof.

DETAILED DESCRIPTION

Figure 1:
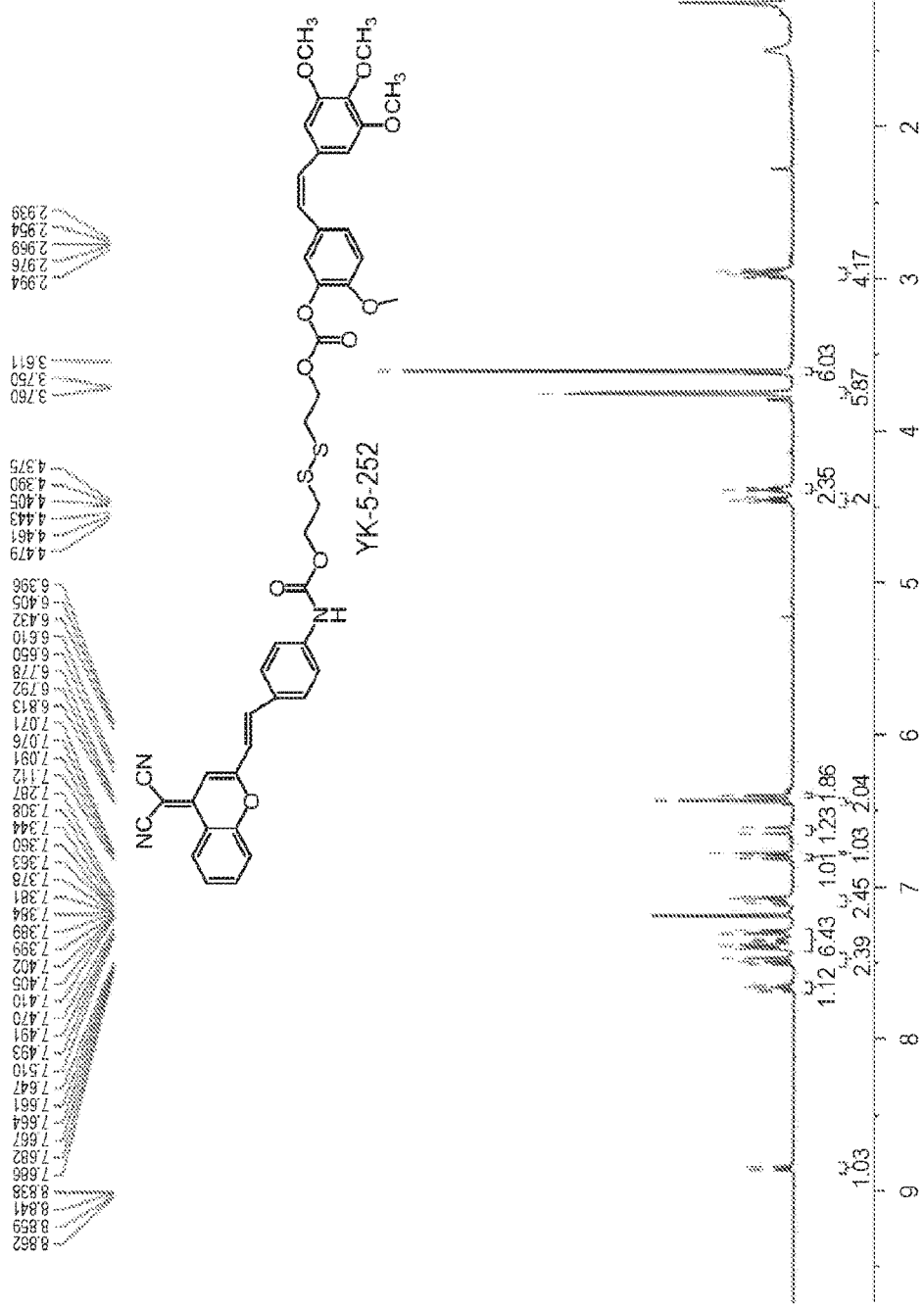
FIG. 1 is a $^1$H-NMR spectrum of YK-5-252.

Described herein is a glutathione-cleavable prodrug and methods for its use. The prodrug can be cleaved by glutathione under, for example, physiological conditions to generate a biologically active agent. The compound described herein is advantageous as the compound is fluorescent and can therefore be monitored within a subject.

I. Compound

A glutathione-cleavable prodrug as described herein is represented by Compound 1, which is also referred to herein as "YK-5-252":

or a pharmaceutically acceptable salt thereof.

II. Methods of Making the Compound

The compound described herein can be prepared in a variety of ways. The compound can be synthesized using various synthetic methods. At least some of these methods are known in the art of synthetic organic chemistry. The compound described herein can be prepared from readily available starting materials. Optimum reaction conditions can vary with the particular reactants or solvent used, but such conditions can be determined by one skilled in the art by routine optimization procedures.

Variations on Compound 1 include the addition, subtraction, or movement of the various constituents as described for each compound. Additionally, compound synthesis can involve the protection and deprotection of various chemical groups. The use of protection and deprotection, and the selection of appropriate protecting groups can be determined by one skilled in the art. The chemistry of protecting groups can be found, for example, in Greene and Wuts, Protective Groups in Organic Synthesis, 3rd. Ed., Wiley & Sons, 2002, which is incorporated herein by reference in its entirety.

Reactions to produce the compound described herein can be carried out in solvents, which can be selected by one of skill in the art of organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatography (HPLC) or thin layer chromatography.

An exemplary method for synthesizing Compound 1 as described herein is provided in Example 1 below.

III. Pharmaceutical Formulations

The compound described herein or pharmaceutically acceptable salts thereof can be provided in a pharmaceutical composition. Depending on the intended mode of administration, the pharmaceutical composition can be in the form of solid, semi-solid or liquid dosage forms, such as, for example, tablets, suppositories, pills, capsules, powders, liquids, or suspensions, preferably in unit dosage form suitable for single administration of a precise dosage. The compositions will include a therapeutically effective amount of the compound described herein or pharmaceutically acceptable salts thereof in combination with a pharmaceutically acceptable carrier and, in addition, may include other medicinal agents, pharmaceutical agents, carriers, or diluents. By pharmaceutically acceptable is meant a material that is not biologically or otherwise undesirable, which can be administered to an individual along with the selected compound without causing unacceptable biological effects or interacting in a deleterious manner with the other components of the pharmaceutical composition in which it is contained.

As used herein, the term carrier encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., Remington: The Science and Practice of Pharmacy, 22d Edition, Loyd et al. eds., Pharmaceutical Press and Philadelphia College of Pharmacy at University of the Sciences (2012). Examples of physiologically acceptable carriers include buffers, such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers, such as polyvinylpyrrolidone; amino acids such as glycine, glutamine, asparagine, arginine or lysine; monosaccharides, disaccharides, and other carbohydrates, including glucose, mannose, or dextrins; chelating agents, such as EDTA; sugar alcohols, such as mannitol or sorbitol; salt-forming counterions, such as sodium; and/or nonionic surfactants, such as TWEEN® (ICI, Inc.; Bridgewater, N.J.), polyethylene glycol (PEG), and PLURONICS' (BASF; Florham Park, N.J.).

Compositions containing the compound described herein or pharmaceutically acceptable salts thereof suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants, such as preserving, wetting, emulsifying, and dispensing agents. Prevention of the action of microorganisms can be promoted by various antibacterial and antifungal agents, for example, parabens, chlorobutanol, phenol, sorbic acid, and the like. Isotonic agents, for example, sugars, sodium chloride, and the like may also be included. Prolonged absorption of the injectable pharmaceutical form can be brought about by the use of agents delaying absorption, for example, aluminum monostearate and gelatin.

Solid dosage forms for oral administration of the compound described herein or pharmaceutically acceptable salts thereof include capsules, tablets, pills, powders, and granules. In such solid dosage forms, the compound described herein or a pharmaceutically acceptable salt thereof is admixed with at least one inert customary excipient (or carrier), such as sodium citrate or dicalcium phosphate, or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others known in the art. They may contain opacifying agents and can also be of such composition that they release the compound in a certain part of the intestinal tract in a delayed manner. Examples of embedding compositions that can be used are polymeric substances and waxes. The compound can also be in microencapsulated form, if appropriate, with one or more of the above-mentioned excipients.

Liquid dosage forms for oral administration of the compound described herein or pharmaceutically acceptable salts thereof include pharmaceutically acceptable emulsions, solutions, suspensions, syrups, and elixirs. In addition to the compound, the liquid dosage forms may contain inert diluents commonly used in the art, such as water or other solvents, solubilizing agents, and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like.

Besides such inert diluents, the composition can also include additional agents, such as wetting, emulsifying, suspending, sweetening, flavoring, or perfuming agents.

Suspensions, in addition to the active compounds, may contain additional agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions of the compound described herein or pharmaceutically acceptable salts thereof for rectal administrations are optionally suppositories, which can be prepared by mixing the compounds with suitable non-irritating excipients or carriers, such as cocoa butter, polyethyleneglycol or a suppository wax, which are solid at ordinary temperatures but liquid at body temperature and, therefore, melt in the rectum or vaginal cavity and release the active component.

Dosage forms for topical administration of the compounds described herein or derivatives thereof include ointments, powders, sprays, and inhalants. The compound described herein or pharmaceutically acceptable salts thereof are admixed under sterile conditions with a physiologically acceptable carrier and any preservatives, buffers, or propellants as may be required. Ophthalmic formulations, ointments, powders, and solutions are also contemplated as being within the scope of the compositions.

The compositions can include the compound described herein and a pharmaceutically acceptable carrier. As used herein, the term pharmaceutically acceptable salt refers to those salts of the compound described herein that are, within the scope of sound medical judgment, suitable for use in contact with the tissues of subjects without undue toxicity, irritation, allergic response, and the like, commensurate with a reasonable benefit/risk ratio, and effective for their intended use, as well as the zwitterionic forms, where possible, of the compounds described herein. The term salts refers to the relatively non-toxic, inorganic and organic acid addition salts of the compound described herein. These salts can be prepared in situ during the isolation and purification of the compound or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, methane sulphonate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. See S. M. Barge et al., J. Pharm. Sci. (1977) 66, 1, which is incorporated herein by reference in its entirety, at least, for compositions taught therein.

Administration of the compound and compositions described herein or pharmaceutically acceptable salts thereof can be carried out using therapeutically effective amounts of the compound and compositions described herein or pharmaceutically acceptable salts thereof as described herein for periods of time effective to treat a disorder. The effective amount of the compound and compositions described herein or pharmaceutically acceptable salts thereof as described herein may be determined by one of ordinary skill in the art and includes exemplary dosage amounts for a mammal of from about 0.5 to about 200 mg/kg of body weight of active compound per day, which may be administered in a single dose or in the form of individual divided doses, such as from 1 to 4 times per day. Alternatively, the dosage amount can be from about 0.5 to about 150 mg/kg of body weight of active compound per day, about 0.5 to 100 mg/kg of body weight of active compound per day, about 0.5 to about 75 mg/kg of body weight of active compound per day, about 0.5 to about 50 mg/kg of body weight of active compound per day, about 0.5 to about 25 mg/kg of body weight of active compound per day, about 1 to about 20 mg/kg of body weight of active compound per day, about 1 to about 10 mg/kg of body weight of active compound per day, about 20 mg/kg of body weight of active compound per day, about 10 mg/kg of body weight of active compound per day, or about 5 mg/kg of body weight of active compound per day.

Those of skill in the art will understand that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition.

The precise dose to be employed in the formulation will also depend on the route of administration, and the seriousness of the disease or disorder, and should be decided according to the judgment of the practitioner and each subject's circumstances. Effective doses can be extrapolated from dose-response curves derived from in vitro or animal model test systems. Further, depending on the route of administration, one of skill in the art would know how to determine doses that result in a plasma concentration for a desired level of response in the cells, tissues and/or organs of a subject.

IV. Methods of Use

Provided herein are methods to treat, prevent, or ameliorate cancer in a subject. The methods include administering to a subject an effective amount of the compound or compositions described herein, or a pharmaceutically acceptable salt thereof. Effective amount, when used to describe an amount of compound in a method, refers to the amount of a compound that achieves the desired pharmacological effect or other biological effect. The compound and compositions described herein or pharmaceutically acceptable salts thereof are useful for treating cancer in humans, including, without limitation, pediatric and geriatric populations, and in animals, e.g., veterinary applications.

Optionally, the cancer is bladder cancer, bone cancer, brain cancer, breast cancer, colon cancer, cervical cancer, gastrointestinal cancer, genitourinary cancer, head and neck cancer, lung cancer, ovarian cancer, pancreatic cancer, renal cancer, skin cancer, or testicular cancer.

Optionally, the breast cancer is triple negative breast cancer. As used herein, triple negative breast cancer (TNBC) refers to a subtype of breast cancer that lacks detectable protein expression of the estrogen receptor (ER) and progesterone receptor (PR) and lacks overexpression of HER2 protein. In other words, TNBC refers to an immunophenotype of breast cancer that is immunologically negative to ER, PR, and HER2.

The methods of treating or preventing cancer in a subject can further comprise administering to the subject one or more additional agents. The one or more additional agents and the compounds described herein or pharmaceutically acceptable salts or prodrugs thereof can be administered in any order, including concomitant, simultaneous, or sequential administration. Sequential administration can be administration in a temporally spaced order of up to several days apart. The methods can also include more than a single administration of the one or more additional agents and/or the compounds described herein or pharmaceutically acceptable salts or prodrugs thereof. The administration of the one or more additional agents and the compounds described herein or pharmaceutically acceptable salts or prodrugs thereof can be by the same or different routes and concurrently or sequentially.

Additional therapeutic agents include, but are not limited to, chemotherapeutic agents. A chemotherapeutic agent is a compound or composition effective in inhibiting or arresting the growth of an abnormally growing cell. Thus, such an agent may be used therapeutically to treat cancer as well as other diseases marked by abnormal cell growth. Illustrative examples of chemotherapeutic compounds include, but are not limited to, bexarotene, gefitinib, erlotinib, gemcitabine, paclitaxel, docetaxel, topotecan, irinotecan, temozolomide, carmustine, vinorelbine, capecitabine, leucovorin, oxaliplatin, bevacizumab, cetuximab, panitumumab, bortezomib, oblimersen, hexamethylmelamine, ifosfamide, CPT-11, deflunomide, cycloheximide, dicarbazine, asparaginase, mitotant, vinblastine sulfate, carboplatin, colchicine, etoposide, melphalan, 6-mercaptopurine, teniposide, vinblastine, antibiotic derivatives (e.g. anthracyclines such as doxorubicin, liposomal doxorubicin, and diethylstilbestrol doxorubicin, bleomycin, daunorubicin, and dactinomycin); antiestrogens (e.g., tamoxifen); antimetabolites (e.g., fluorouracil (FU), 5-FU, methotrexate, floxuridine, interferon alpha-2B, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cisplatin, vincristine and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chlorambucil, mechlorethamine (nitrogen mustard) and thiotepa); and steroids (e.g., bethamethasone sodium phosphate).

The methods and compounds as described herein are useful for both prophylactic and therapeutic treatment. For prophylactic use, a therapeutically effective amount of the compound and compositions or pharmaceutically acceptable salts thereof as described herein are administered to a subject prior to onset (e.g., before obvious signs of cancer), during early onset (e.g., upon initial signs and symptoms of cancer), or after the development or treatment of cancer (e.g., to prevent recurrence or metastasis). Prophylactic administration can occur for several days to years prior to the manifestation of symptoms of cancer. Therapeutic treatment involves administering to a subject a therapeutically effective amount of the compounds and compositions or pharmaceutically acceptable salts thereof as described herein after cancer is diagnosed.

The compounds described herein are useful in treating diseases that include the overexpression of glutathione.

The methods and compound described herein are also useful in inhibiting angiogenesis in a subject. The methods of inhibiting angiogenesis in a subject includes administering to the subject an effective amount of the compound described herein. The subject can be a subject that has cancer, such as a triple negative breast cancer. Optionally, the cancer overexpresses glutathione.

The methods and compound described herein are also useful in inhibiting tubulin polymerization in a cell. The methods of inhibiting tubulin polymerization in a cell includes contacting the cell with an effective amount of the compound described herein. The cell can be a cancer cell, such as a triple negative breast cancer cell. Optionally, the cell is a cell that overexpresses glutathione. Optionally, the contacting is performed in vivo. Optionally, the contacting is performed in vitro.

Also described herein are methods of delivering combretastatin A-4 (CA-4) to a cell. The methods of delivering CA-4 to a cell include contacting a cell containing glutathione with a compound as described herein. Once the compound is in the cell, glutathione cleaves the disulfide bond in the compound to form CA-4. The cell can be a cancer cell, such as a triple negative breast cancer cell. Optionally, the cell is a cell that overexpresses glutathione. The contacting can be performed in vivo or in vitro.

Further described herein are methods of imaging a glutathione containing cell or population of cells in a subject. The methods of imaging include administering to the subject the compound described herein and detecting fluorescence in the subject. The fluorescence indicates a glutathione containing cell or population of cells. The detecting step can include imaging methods such as positron emission tomography (PET), single-photon emission computed tomography (SPECT), magnetic resonance imaging (MRI), or X-ray. Such imaging methods are useful for assessing the extent of disease and/or the target of the therapeutic agent. Imaging methods can also be used to determine the efficacy of the therapeutic agent. Such imaging can be performed concomitantly with a method of treatment using the same compound. One of skill in the art may adjust the dosage for imaging, as compared to therapeutic uses. Such adjustment is within the skill of one of ordinary skill in the art.

V. Kits

Also provided herein are kits for treating or preventing cancer in a subject. A kit can include the compound or compositions described herein. For example, a kit can include Compound 1 or a salt thereof. A kit can further include one or more additional agents, such as a chemotherapeutic agent. A kit can include an oral formulation of any of the compounds or compositions described herein. A kit can additionally include directions for use of the kit (e.g., instructions for treating a subject), a container, a means for administering the compound or compositions (e.g., a syringe), and/or a carrier. A kit can include multiple metered dosages for a course of treatment with Compound 1, with or without any additional therapeutic agent.

As used herein the terms treatment, treat, or treating refer to a method of reducing one or more symptoms of a disease or condition. Thus in the disclosed method, treatment can refer to a 10%, 20%, 30%, 40%, 50%, 60%, 70%, 80%, 90%, or 100% reduction in the severity of one or more symptoms of the disease or condition. For example, a method for treating a disease is considered to be a treatment if there is a 10% reduction in one or more symptoms or signs (e.g., size of the tumor or rate of tumor growth) of the disease in a subject as compared to a control. As used herein, control refers to the untreated condition (e.g., the tumor cells not treated with the compound and compositions described herein). Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition.

As used herein, the terms prevent, preventing, and prevention of a disease or disorder refer to an action, for example, administration of a composition or therapeutic agent, that occurs before or at about the same time a subject begins to show one or more symptoms of the disease or disorder, which inhibits or delays onset or severity of one or more symptoms of the disease or disorder. For example, the method is considered to be a prevention if there is a reduction or delay in onset, incidence, severity or recurrence of cancer, or one or more symptoms of cancer (e.g., tumor growth) in a subject susceptible to cancer compared to control subjects susceptible to cancer that did not receive a compound as described herein. The reduction or delay in onset, incidence, severity, or recurrence of infection or cancer can be 10%, 20%, 30%, 40%, 50%, 60%, 70%, 80%, 90%, 100%, or any percent reduction in between 10% and 100% as compared to native or control levels.

As used herein, references to decreasing, reducing, or inhibiting include a change of 10%, 20%, 30%, 40%, 50%, 60%, 70%, 80%, 90% or greater as compared to a control level. Such terms can include, but do not necessarily include, complete elimination.

As used herein, subject means both mammals and non-mammals. Mammals include, for example, humans; non-human primates, e.g., apes and monkeys; cattle; horses; sheep; rats; mice; pigs; and goats. Non-mammals include, for example, fish and birds.

Throughout this application, various publications are referenced. The disclosures of these publications in their entireties are hereby incorporated by reference into this application.

The examples below are intended to further illustrate certain aspects of the methods and compositions described herein, and are not intended to limit the scope of the claims.

EXAMPLES

Example 1: Synthesis

A novel near-infrared (NIR) fluorescent theranostic anti-cancer agent, referred to herein as YK-5-252 or Compound 1, was designed and synthesized. The fluorophore and its cleavable disulfide linker were successfully synthesized and its final structure was characterized by NMR, FIRMS, and flow cytometry fluorescent spectra analysis. The designed drug with linked disulfide bond can be cleaved by intracellular glutathione (GSH). Because cancer cells have much higher GSH concentrations than normal cells, this GSH-cleavable prodrug holds promising therapeutic efficacy. Near-infrared photons can deeply penetrate the skin and tissue with minimal damage. An in vitro cytotoxicity assay revealed YK-5-252 is much less toxic than its linked parent drug. Intracellular co-localization showed that in cancer cells, the drug can be cleaved to release the parent drug, offering potential selectivity and specificity than its parent drug. Because of its NIR fluorescent property, it also offers an excellent ability for tracking drug release in vivo. The designed drug serves as both a diagnostic and a treatment.

Scheme 1 provides a method for synthesizing YK-5-252.

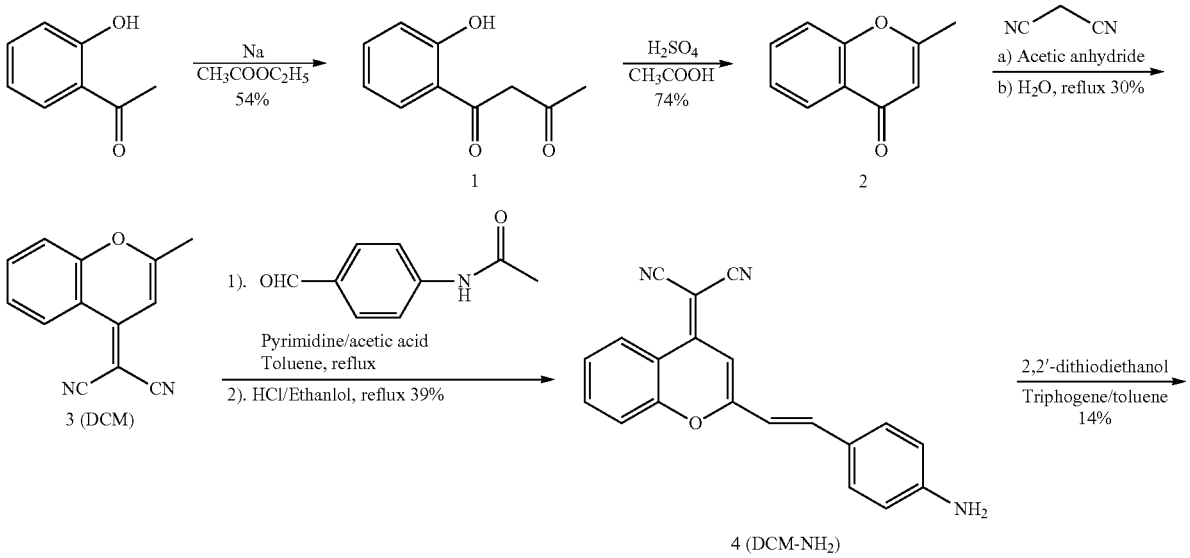

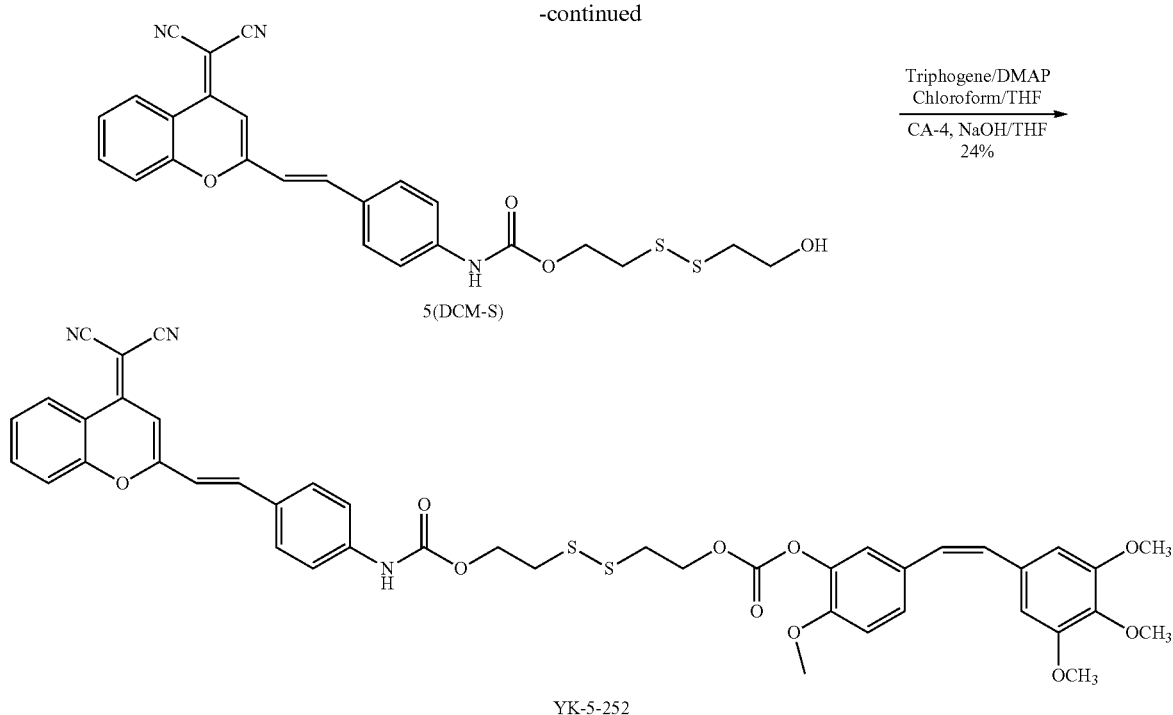

5(DCM-S)

YK-5-252

Materials and Methods

All reagents and solvents were purchased from commercial suppliers and used as received unless noted otherwise. Flash column chromatography separations were done on a Biotage SP1 system monitoring at 254 and 310 nm. NMR spectra were recorded on a Varian 400 spectrometer at 25° C., operating at 400 MHz for $^1$H and 100 MHz for $^{13}$C NMR. The chemical shifts are expressed in ppm downfield from TMS as an internal standard. Reactions were monitored by thin-layer chromatography (TLC) on silica gel 60 glass slides. The structure of the synthesized compounds follows unequivocally from the mode of synthesis and the m/z values found in their low- and high-resolution mass spectra, TLC and NMR spectroscopy verified the purity.

The GSH-activatable fluorophoric prodrug was synthesized by combining a NIR fluorophoric agent with a GSH-activatable disulfide linker, which in turn was conjugated to the anticancer agent combretastatin A-4 (CA-4). The following steps were followed: 1) 2-(2-methyl-4H-chromen-4-ylidene) malononitrile (DCM) synthesis; 2) NIR fluorophore DCM-NH$_2$ synthesis; 3) conjugation of DCM-NH$_2$ with a GSH-cleavable disulfide (S—S) linker; and 4) connection with CA-4.

Synthesis of 1-(2-hydroxyphenyl)butane-1,3-dione (1)

1-(2-hydroxyphenyl)ethanone (5.0 g, 36.2 mmol) was dissolved in 100 mL ethyl acetate, and then sodium (4.0 g, 0.17 mmol) was added into the solution. The resulting mixture was stirred at room temperature for 3 hours. The solid was filtered off and dissolved in 50 mL water, and the pH value was adjusted to neutral using 6 N HCl. The product was extracted with ethyl acetate and the organic layers were dried over Na$_2$SO$_4$. The solvent was removed under vacuo to produce a brown solid (3.6 g, 54%), which was directly used for the next step without further purification.

Synthesis of 2-methyl-4H-chromen-4-one (2)

To a solution of 1 (3.6 g, 20.2 mmol) in acetic acid (35 mL) was added dropwise 3.0 mL of sulfuric acid. The mixture was refluxed for 30 minutes and then poured into ice water. The aqueous solution was neutralized with saturated aqueous Na$_2$CO$_3$ and then extracted with ethyl acetate. The organic layers were dried over Na$_2$SO$_4$, filtered, and concentrated to yield the crude product as a red solid. The crude product was purified by silica column chromatography using a mixture of hexanes/ethyl acetate as the eluent to afford the product as a pale yellow solid (2.3 g, 74%).

Synthesis of 2-(2-methyl-4H-chromen-4-ylidene)malononitrile (3, DCM)

Malononitrile (1.0 g, 15.0 mmol) and 2 (2.0 g, 12.5 mmol) were dissolved in 15 mL of acetic anhydride. The solution was refluxed for 5 hours and an additional 300 mg of malononitrile was added and refluxed for 4 hours. The solvent was evaporated in vacuo to dryness, water (40 mL) was added, and the mixture was refluxed for 0.5 hours. The water was removed to dryness and the crude product was applied to a silica column and purified using hexane/ethyl acetate as the eluent. Compound 3 (DCM) was obtained as an orange solid (0.78 g, 30%).

Synthesis of (E)-2-(2-(4-aminostyryl)-4H-chromen-4-ylidene)malononitrile (5, DCM-NH$_2$)

DCM (252 mg, 1.20 mmol) and 4-acetamido benzaldehyde (147 mg, 1.2 mmol) were dissolved in toluene (40 mL). Piperidine (0.6 mL) and acetic acid (0.6 mL) were added and the mixture was refluxed for 3 hours. The orange solid that formed was filtered off and concentrated HCl/ethanol (45 mL, 2:1) was added. The mixture was refluxed for 2 hours.

The mixture was then neutralized with saturated aqueous $Na_2CO_3$ to pH 8 and then extracted with ethyl acetate. The ethyl acetate layers were combined, washed with brine, and dried over $Na_2SO_4$. The organic solvent was removed in vacuo and the residue was purified by silica chromatography with hexane/ethyl acetate as the eluent. Compound 5 was obtained as a deep red solid (146 mg, 39%).

Synthesis of 6 (DCM-S)

To a mixture of DCM-$NH_2$ (20 mg, 0.064 mmol) and triphosgene (76 mg, 0.26 mmol) in dry toluene (10 mL) was added N,N-diisopropylethylamine (DIEA; 132.3 mg, 1.0 mmol) dropwise at room temperature. The mixture was refluxed for 3 hours. The unreacted phosgene was removed by flushing with $N_2$ gas. 2, 2'-Dithiodiethanol (98.7 mg, 0.64 mmol) in $CH_2Cl_2$/THF (1:1, 4 mL) was then added and the mixture was stirred at room temperature overnight. The solvent was removed and the crude product was purified by silica column chromatography to afford an orange-yellow solid as the product DCM-S (15 mg, 48%).

Synthesis of Final Product YK-5-252

A mixture of DCM-S (20 mg, 0.04 mmoL), triphosgene (5 mg, 0.016 mmoL), and 4-dimethylaminopyridine (DMAP; 6 mg, 0.049 mmoL) in chloroform/THF (1:1, 10 mL) was stirred at room temperature for 3 hours. Then the solvent was evaporated in vacuo. The residue was dissolved in THF (5 mL) and a chilled solution of CA-4 (13 mg, 0.04 mmol) in 0.09 mL of 0.5 M NaOH and 1 mL THF was added. The reaction mixture was stirred at room temperature overnight. The mixture was neutralized with saturated aqueous $NaHCO_3$ to pH of 6-7, concentrated, and purified by silica chromatography (20% Toluene-EtOAc as the eluent) to afford a dark red solid (8 mg, 24%). The $^1$H-NMR spectrum for the compound is shown in FIG. 1.

Figure 2:
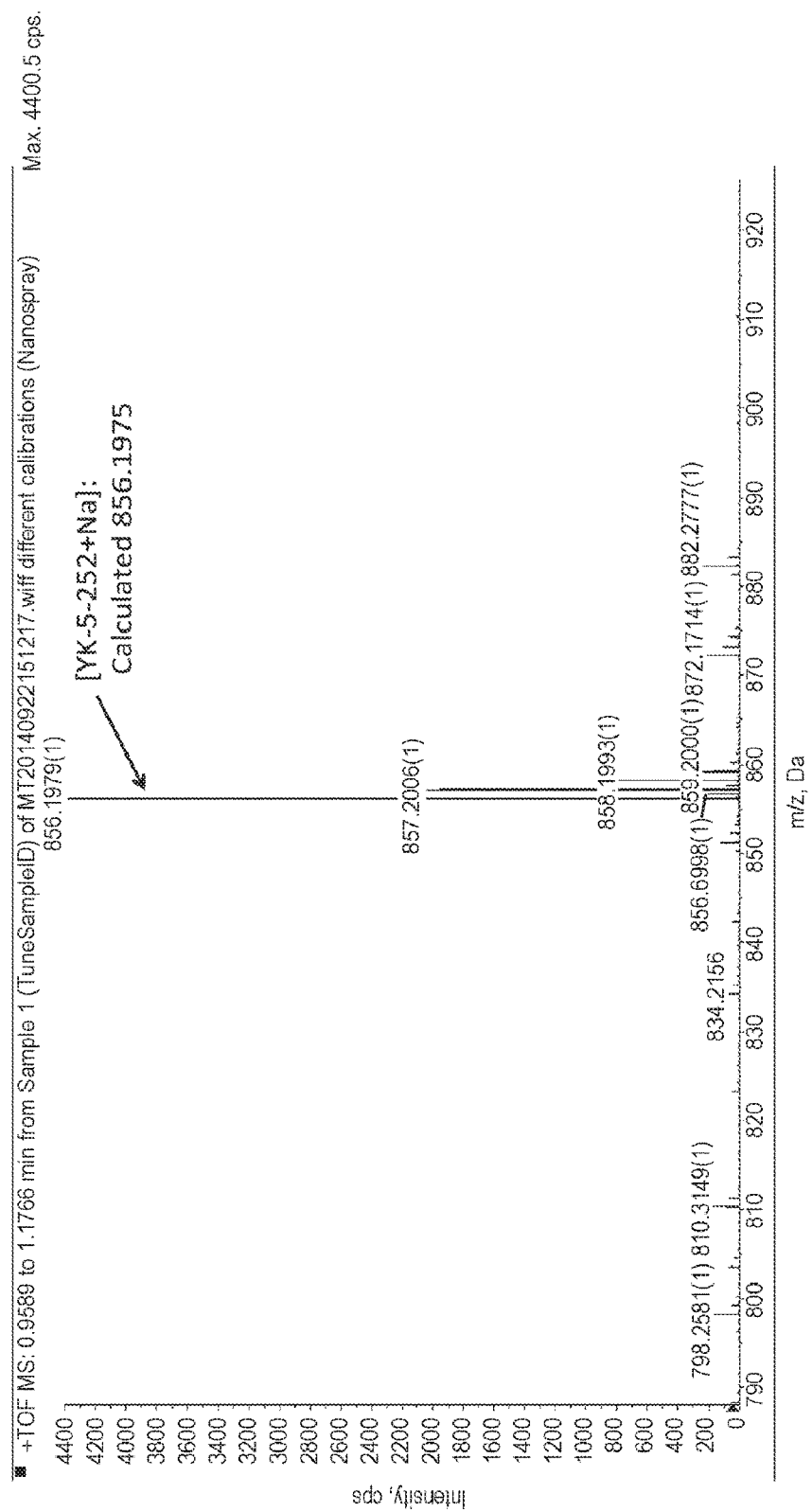
FIG. 2 is a mass spectrometry plot of YK-5-252.
Figure 3:
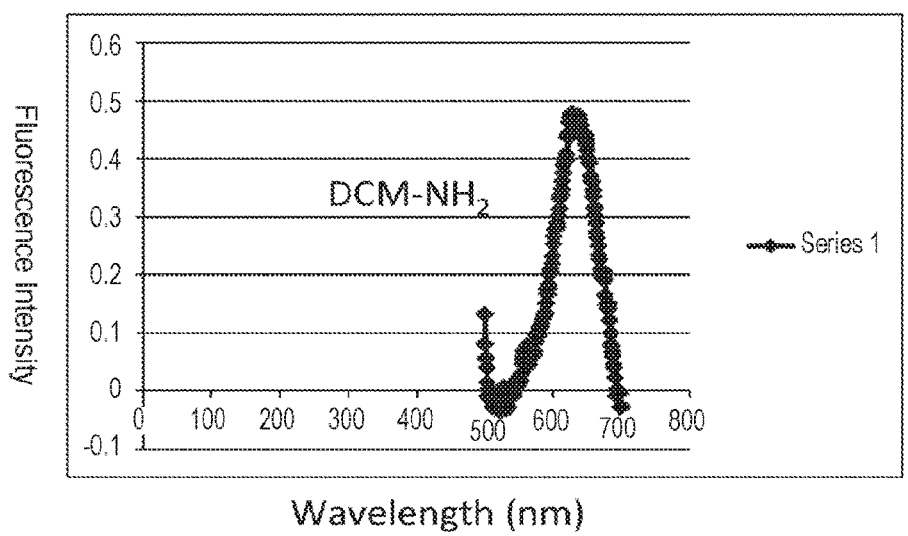
FIG. 3 is a fluorescence spectrum for (E)-2-(2-(4-aminostyryl)-4H-chromen-4-ylidene)malononitrile (DCM-NH$_2$).
Figure 4:
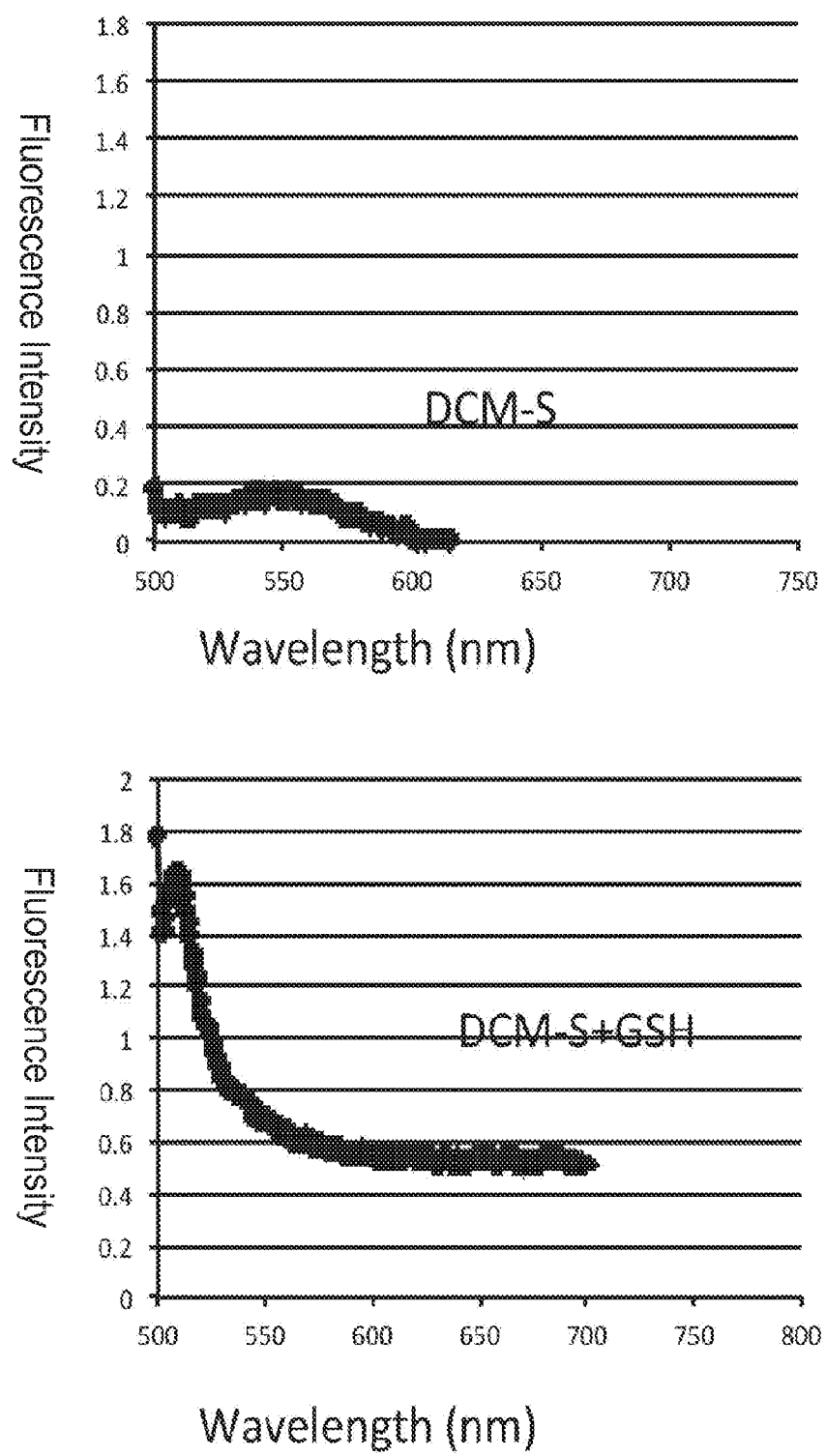
FIG. 4 contains fluorescence spectra for DCM-S (top panel) and for DCM-S and glutathione (bottom panel).
Figure 5:
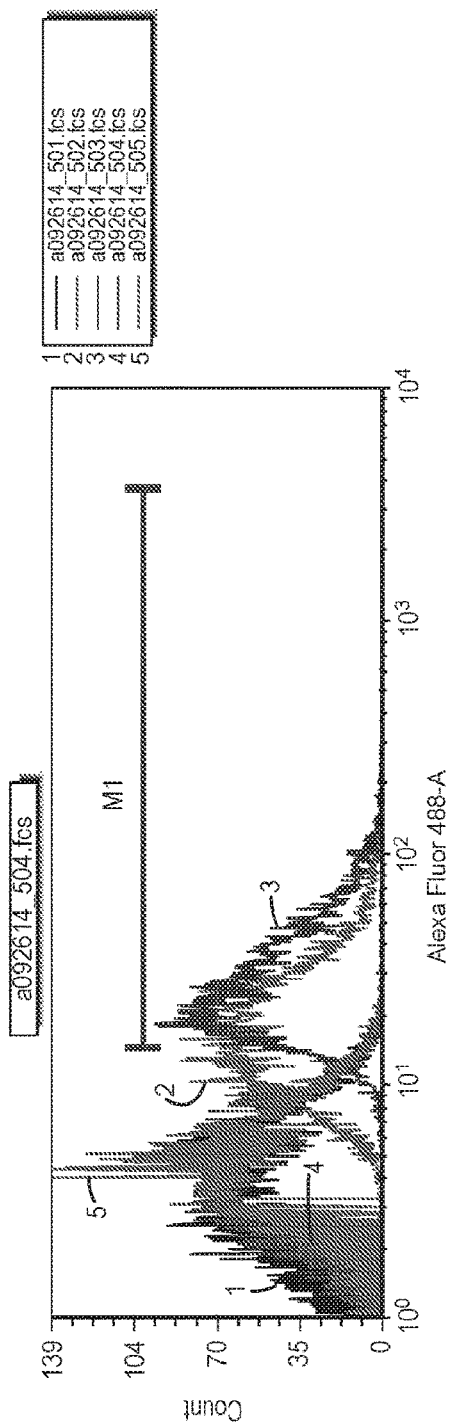
FIG. 5 contains flow cytometry analysis plots for YK-5-252 and CA-4 after 24 hours and 48 hours.

In this study, a novel NIR-fluorophoric compound (YK-5-252) was successfully synthesized. The chemical structure was confirmed by NMR analysis (FIG. 1) and high resolution mass spectra analysis (HRMS) (FIG. 2). The fluorescent properties were also confirmed by fluorescent flow cytometry analysis. DCM-$NH_2$ can be detected in the long wavelength (600-700 nm) (FIG. 3). After being linked with a disulfide bond DCM-S, the fluorescent became very weak (FIG. 4), however when GSH was added, the fluorescent intensity increased sharply (FIG. 5). This shows that upon linkage to a disulfide bond, it will become cleavable in vitro or in vivo system with existence of GSH. The results indicate that a quenched, fluorophore-enhanced, and GSH-activatable form of CA-4 can be created in quantities suitable enough for the future drug conjugation.

As described herein, a NIR probe conjugated with combretastatin A-4 (CA-4) through a disulfide linker was successfully synthesized.

Example 2: Assays

Figure 7:
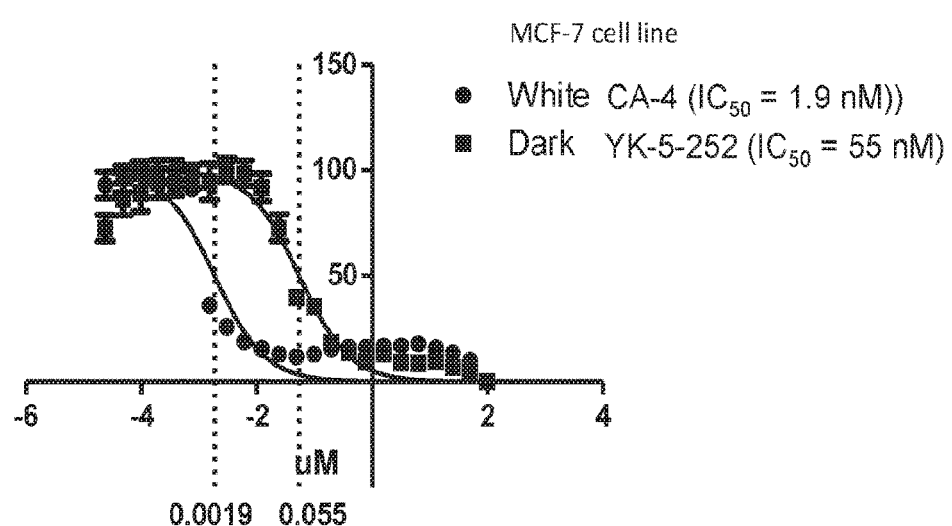
FIG. 7 contains plots for use in calculating the IC$_{50}$ values for YK-5-252 and CA-4 in a MCF-7 cell line.
Figure 8:
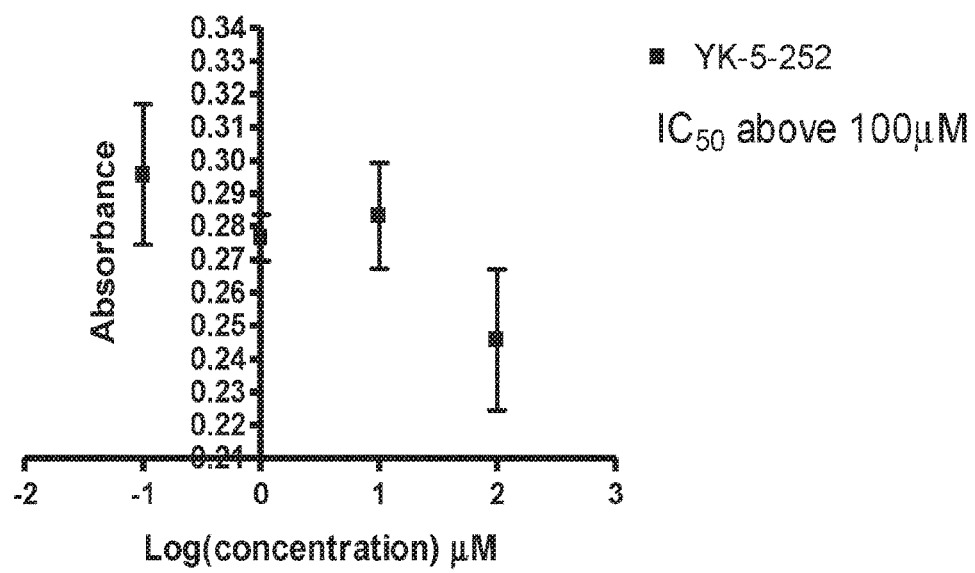
FIG. 8 contains plots for use in calculating the IC$_{50}$ values for YK-5-252 and CA-4 in a MCF-10A cell line.
Figure 8:
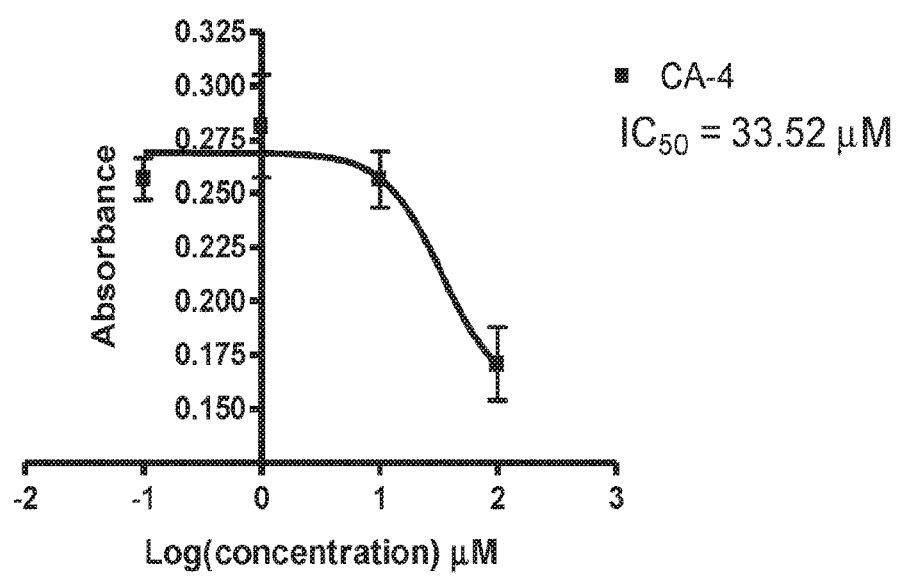
Figure 9:
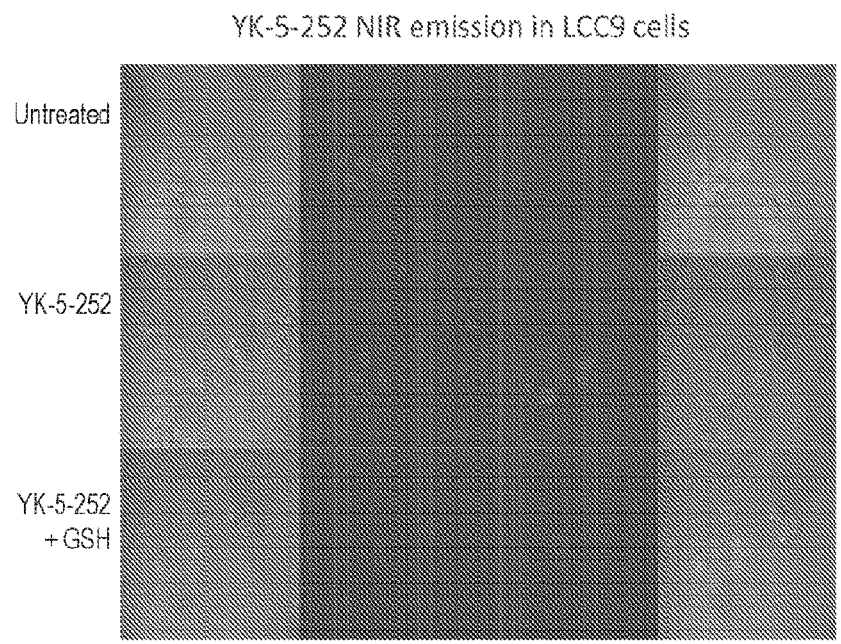
FIG. 9 contains pictures depicting the intracellular colocalization of YK-5-252, with and without glutathione present, in LCC9 cells.
Figure 10:
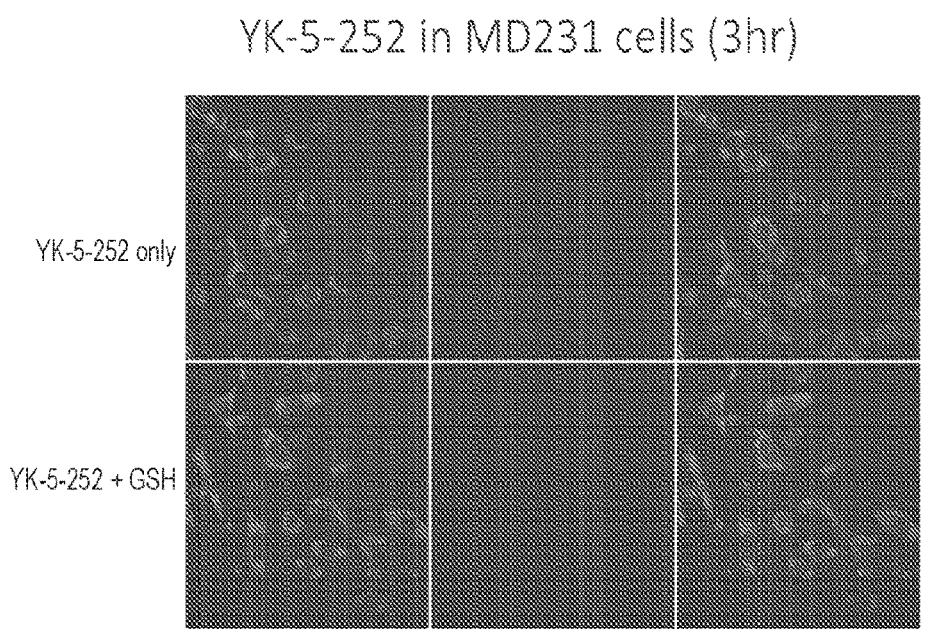
FIG. 10 contains pictures depicting the intracellular colocalization of YK-5-252, with and without glutathione present, in MD231 cells.

YK-5-252, the designed drug with linked disulfide bond described above, can be cleaved by intracellular glutathione (GSH). Cancer cells have a much higher GSH concentration than normal cells; therefore, this GSH-cleavable prodrug holds promising therapeutic efficacy. Near-infrared photons can deeply penetrate the skin and tissue with minimal damage. An in vitro cytotoxicity assay revealed YK-5-252 is much less toxic than its linked parent drug (FIGS. 7 and 8). Intracellular colocalization showed that in cancer cells the drug would be able to be cleaved to release the parent drug, offering potential selectivity and specificity than its parent drug (FIGS. 9 and 10). Due to its NIR fluorescent property, the compound also offers an excellent ability for tracking drug release in vivo.

Example 3: YK-5-252 Fluorescent Properties

Figure 11:
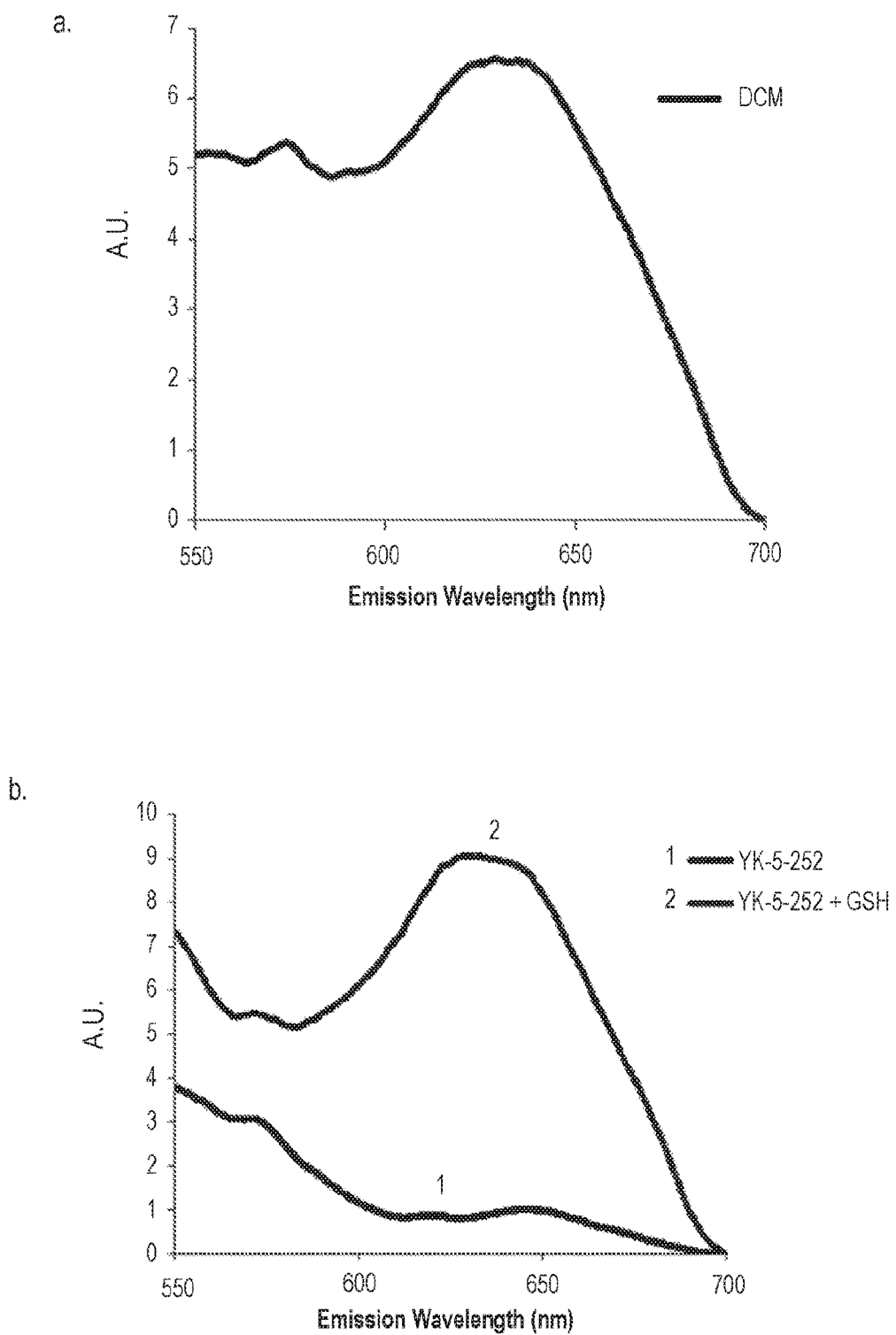
FIG. 11 contains emission spectra of compounds described herein. Panel A shows an emission spectrum of DCM (1 mM). Panel B shows an emission spectrum of YK-5-252 (1 mM) alone (bottom line) and YK-5-252 (1 mM) in the presence of GSH (250 mM; pH 8) in DMSO/PBS solution (50/50, v/v) (top line).

The fluorescence properties and ability to be activated via GSH cleavage of YK-5-252 were evaluated. DCM-$NH_2$ has a NIR fluorescence emission at 650 nm with an excitation of 492 nm (FIG. 11, panel a). However, when conjugated with CA-4, YK-5-252 has no NIR emission (FIG. 11, panel b). This can be due to the loss of electron donating ability of the amine group when attached to the linker. To ascertain the stability of YK-5-252 toward GSH, fluorescence was monitored in the presence of GSH. Treatment with GSH (250 mM; pH 8) resulted in an emission at 650 nm (FIG. 11, panel b).

Example 4: Live Cell Imaging

Figure 12:
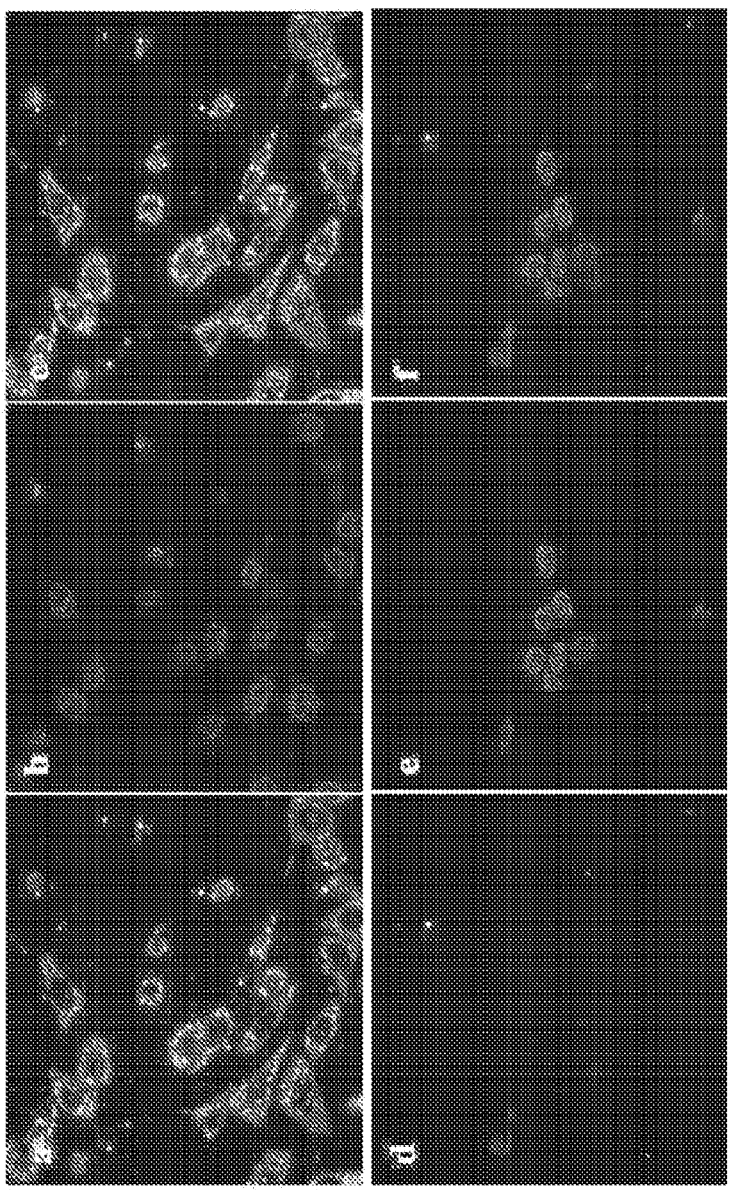
FIG. 12, panel (a) contains a confocal microscopy image of MDA-MB-231 cells (triple negative breast cancer cells) treated with YK-5-252 (1 micromolar) for 1 hour. Panel (b) contains a nuclear staining image of the cells with Hoesht dye. Panel (c) contains a merged image of panels (a) and (b). Panel (d) contains a confocal microscopy image of MCF10A (normal breast cells) treated with YK-5-252 (1 micromolar) for 1 hour. Panel (e) contains a nuclear stained image of the cells with Hoescht dye. Panel (f) contains a merged image of panels (d) and (e).

To test the ability of YK-5-252 to selectively release CA-4 in cancer cells, the presence of DCM was monitored through confocal microscopy. After 1 hour of treatment, the fluorescence was observed in higher quantities in the triple negative breast cancer (TNBC) cells (MDA-MB-231; FIG. 12, panels a-c) versus normal breast cells (MCF10A; FIG. 12, panels d-f). This demonstrates that YK-5-252 was rapidly cleaved in vitro by TNBC cells, which produces a higher concentration of GSH. Also this experiment confirms the utility of YK-5-252 to monitor drug delivery and release in vivo.

Example 5: Flow Cytometry

Figure 13:
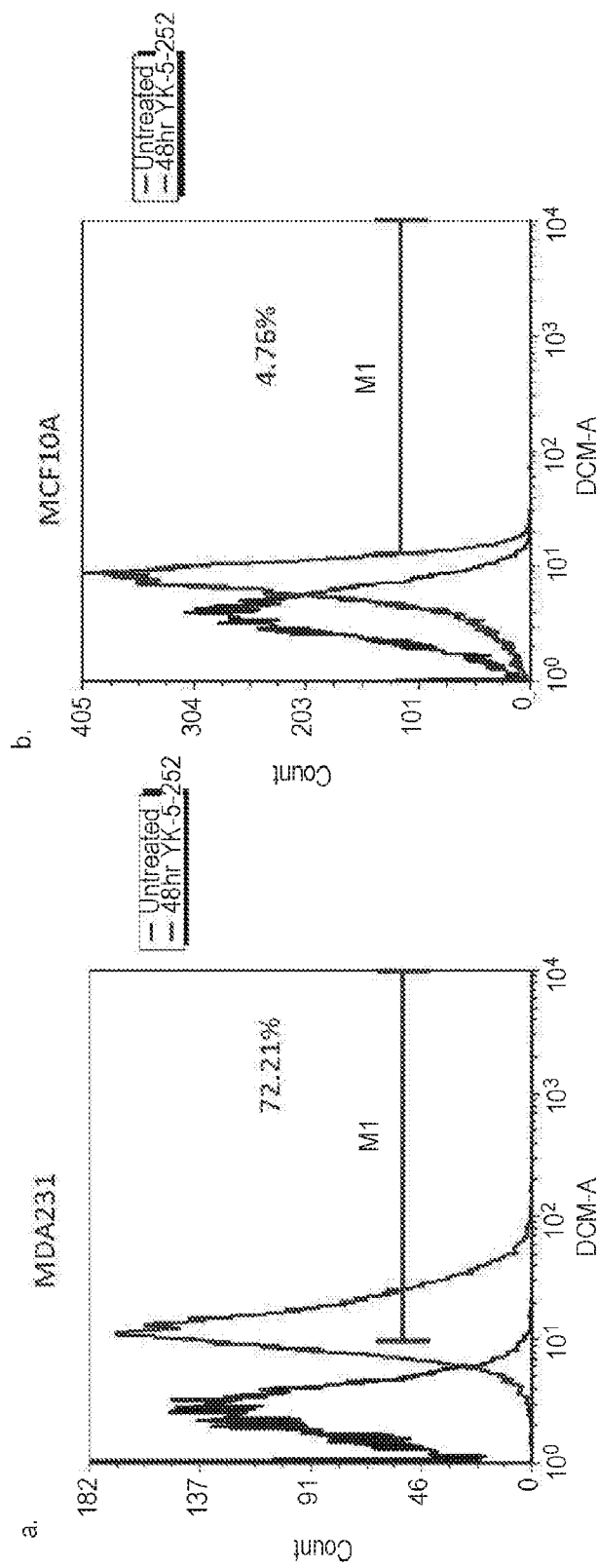
FIG. 13 contains flow cytometry spectra depicting the cellular uptake of YK-5-252. Panel (a) shows the spectrum depicting cellular uptake of YK-5-252 in triple negative breast cancer cells (MDA-MB-231) after 48 hours of treatment. Panel (b) shows the spectrum depicting cellular uptake of TK-5-252 in normal breast cancer cells (MCF10A) after 48 hours of treatment.
Figure 14:
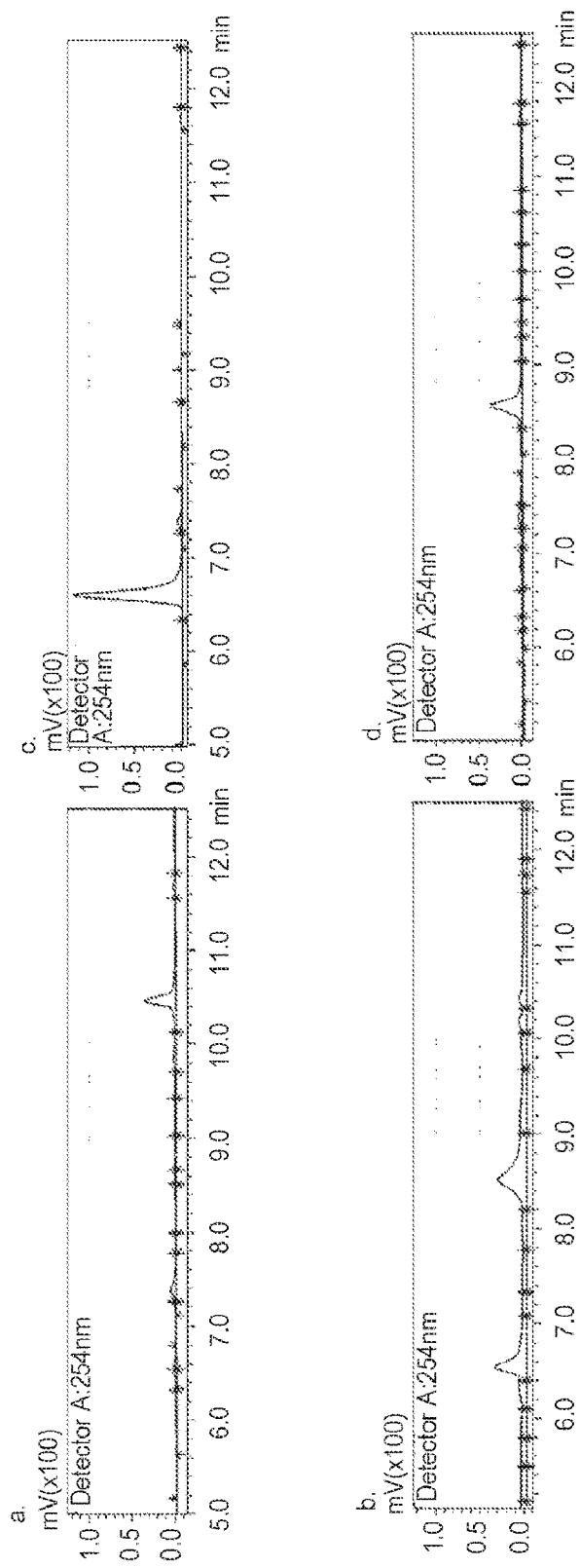
FIG. 14 contains HPLC traces. Panel (a) is a trace of YK-5-252 (200 μM). Panel (b) is a trace of YK-5-252 (200 μM) and glutathione (GSH; 50 mM). Panel (c) is a trace of CA-4 (200 μM). Panel (d) is a trace of DCM (200 μM). The retention time for YK-5-252 was found to be 10.5 minutes (Panel (a)). After treatment with GSH (Panel (b)), the YK-5-252 peak at 10.5 minutes disappeared while two new peaks at 6.8 and 8.6 minutes appears which corresponds to the release of CA-4 and DCM-NH$_2$, respectively (Panels (c) and (d)).
Figure 15:
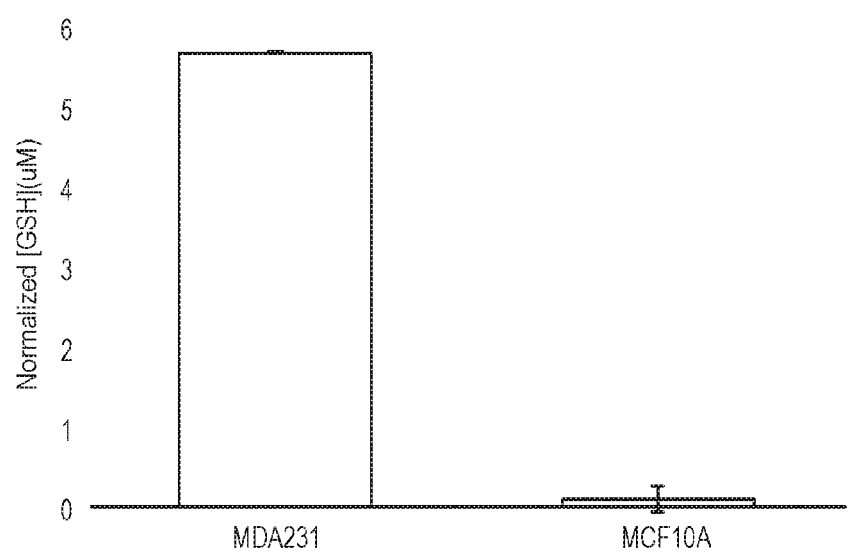
FIG. 15 is a graph showing the concentration of GSH produced by triple negative breast cancer cells (MDA-MB-231) and normal breast cells (MCF10A). Using a colorimetric assay, the GSH concentration in triple negative breast cancer cells was found to be 20 times greater than the concentration in normal cells.

To further investigate the in vivo activation of YK-5-252, fluorescence-activated cell sorting (FACS) was used. Cells were treated with YK-5-252 for 48 hours. After treatment, FACS analysis was conducted to determine how much of the cell population has DCM-$NH_2$ present. FACS analysis showed that 72% of the TNBC cells (MDA-MB-231) contained DCM-$NH_2$ (FIG. 13, panel a) whereas only about 5% of normal cells (MCF10A) (FIG. 13, panel b) contained the fluorophore. This experiment, along with the imaging results, indicates that TNBC cells release more DCM-$NH_2$ than normal cells. HPLC analysis confirmed that CA-4 release is concurrent with the release of DCM-$NH_2$ in a traceless manner (FIG. 14, panels (a-d)). The difference in prodrug cleavage in cancer cells versus normal cells is due to the higher levels of GSH produced in cancer cells. As shown in FIG. 15, GSH levels in MDA-MB-231 cancer cells were significantly higher than levels in MCF10A normal cells.

Example 6: Tubulin Polymerization

Figure 6:
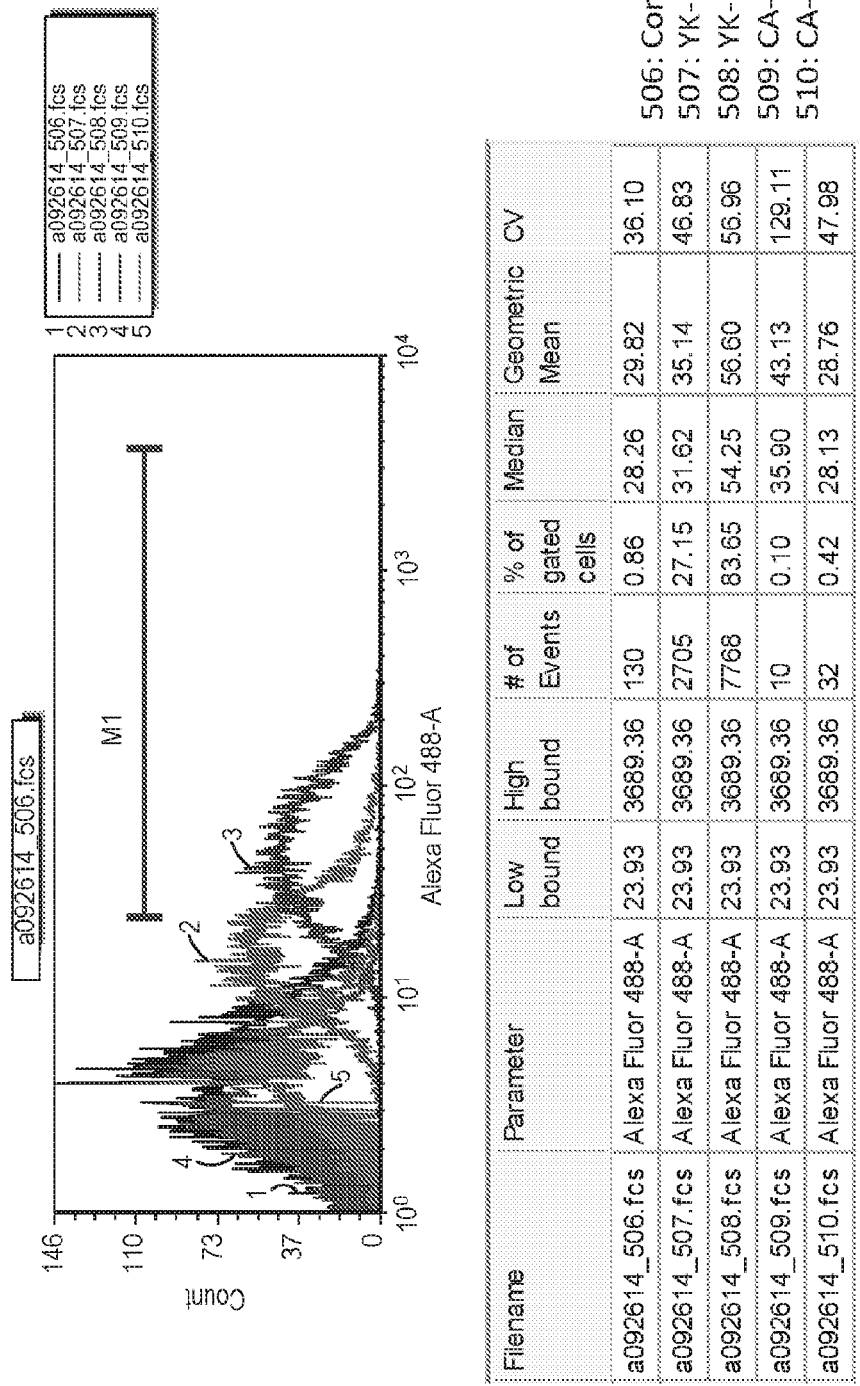
FIG. 6 contains flow cytometry analysis plots for YK-5-252 and CA-4 after 24 hours and 48 hours.
Figure 16:
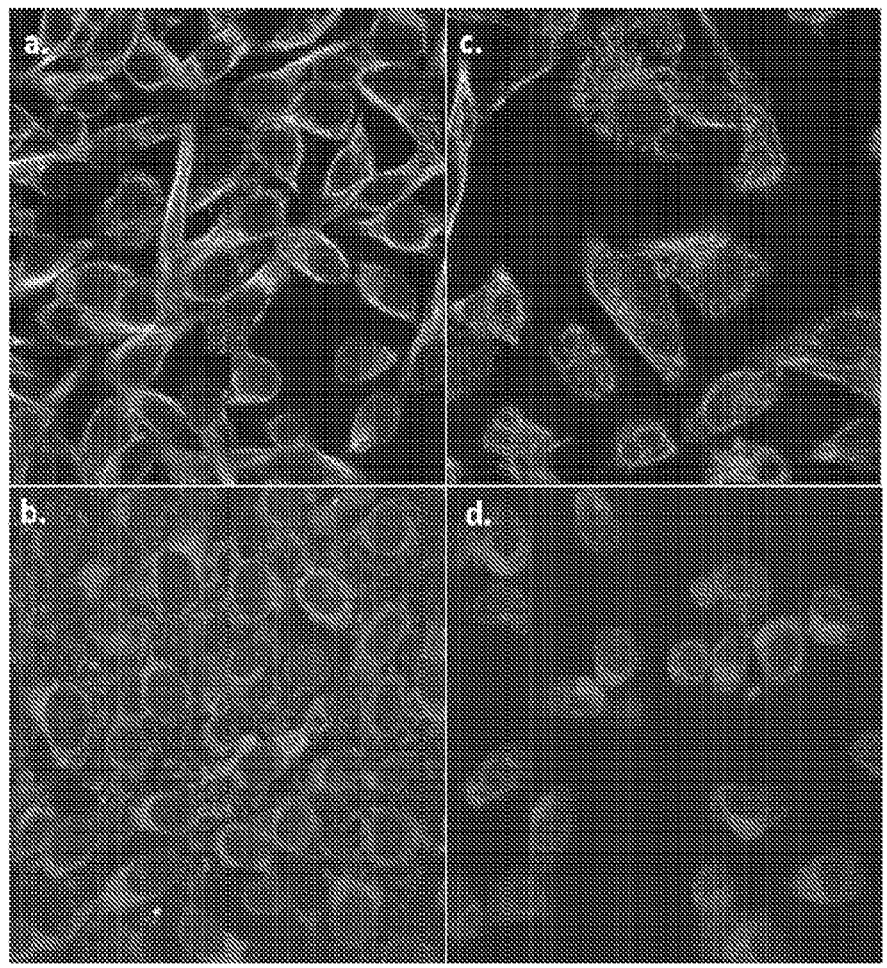
FIG. 16 shows the immunofluorescence staining of tubulin in triple negative breast cancer cells (MDA-MB-231). Panel (a) shows the cells treated with YK-5-252 (50 nM; 1 hr). Panel (b) shows the cells treated with CA-4 (50 nM; 1 hr). Panel (c) shows the cells treated with YK-5-252 (50 nM; 6 hr). Panel (d) shows the cells treated with CA-4 (50 nM; 6 hr).

To determine the biological effect of YK-5-252, its mechanism of action was determined through immunofluorescence staining. Treatment of TNBC cells with YK-5-252 (50 nM) did not cause disruption of tubulin polymerization after 1 hour of treatment (FIG. 16, panel (a)) whereas CA-4 (50 nM) completely inhibited tubulin polymerization within 1 hour (FIG. 6, panels (b) and (d)). However, after 6 hours of treatment, YK-5-252 began to disrupt tubulin polymerization (FIG. 16, panel (c)). This shows that YK-5-252 reduces the toxicity of CA-4 by slowing the release of CA-4 in cells (Table 1).

TABLE 1

|  | YK-5-252 (micromolar) | CA-4 (micromolar) |
|---|---|---|
| MCF10A | 0.01918 <br> ($CI_{95}$ = <br> 0.004844 to 0.07596) | $<10^{-6}$ |
| MDA-MB-231* | 0.04033 <br> ($CI_{95}$ = <br> 0.0168 to 0.0968) | 0.002806 <br> ($CI_{95}$ = <br> 0.000641 to 0.01229) |

*Values determined after 72 hours of treatment

Example 7: Cell Proliferation

To evaluate the toxicity of YK-5-252 in cells, the inhibition of cell proliferation was measured in normal cells (MCF10A) and TNBC cells (MDA-MB-231). In normal cells, YK-5-252 had a $GI_{50}$ of approximately 19.2 nM whereas CA-4 has a $GI_{50}$ less than 1 pM. In TNBC cells, YK-5-252 had a $GI_{50}$ of 40.3 nM whereas CA-4 had a $GI_{50}$ of 28.1 nM. The lower $GI_{50}$ of CA-4 in normal and TNBC cells indicates that YK-5-252 reduces the toxicity of CA-4. However both CA-4 and YK-5-252 are highly potent in normal cells. This lack of selectivity can be attributed to the toxicity of YK-5-252.

The compounds and methods of the appended claims are not limited in scope by the specific compounds and methods described herein, which are intended as illustrations of a few aspects of the claims and any compounds and methods that are functionally equivalent are within the scope of this disclosure. Various modifications of the compounds and methods in addition to those shown and described herein are intended to fall within the scope of the appended claims. Further, while only certain representative compounds, methods, and aspects of these compounds and methods are specifically described, other compounds and methods are intended to fall within the scope of the appended claims. Thus, a combination of steps, elements, components, or constituents can be explicitly mentioned herein; however, all other combinations of steps, elements, components, and constituents are included, even though not explicitly stated.

What is claimed is:

1. A compound of the following formula:

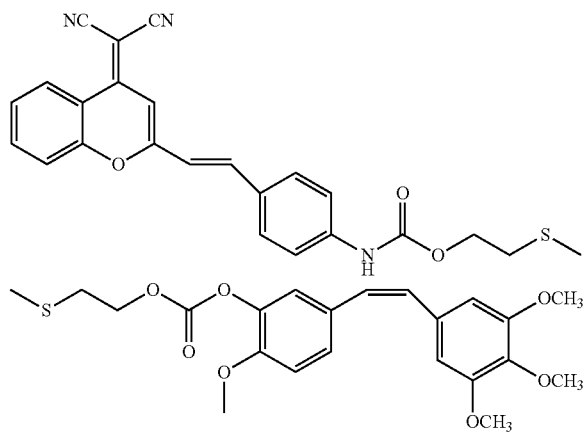

or a pharmaceutically acceptable salt thereof.

2. A composition comprising a compound of claim 1 and a pharmaceutically acceptable carrier.

3. A kit comprising a compound of claim 1.

4. A method of treating cancer in a subject, comprising administering to the subject an effective amount of a compound of claim 1, wherein the cancer is bladder cancer, bone cancer, brain cancer, breast cancer, colon cancer, cervical cancer, gastrointestinal cancer, genitourinary cancer, head and neck cancer, lung cancer, ovarian cancer, pancreatic cancer, renal cancer, skin cancer, or testicular cancer.

5. The method of claim 4, wherein the cancer is breast cancer.

6. The method of claim 5, wherein the breast cancer is triple negative breast cancer.

7. A method of inhibiting angiogenesis in a subject, comprising administering to the subject an effective amount of a compound of claim 1.

8. The method of claim 7, wherein the subject has cancer.

9. The method of claim 8, wherein the cancer is triple negative breast cancer.

10. The method of claim 8, wherein the cancer overexpresses glutathione.

11. A method of inhibiting tubulin polymerization in a cell, comprising contacting the cell with an effective amount of a compound of claim 1.

12. The method of claim 11, wherein the cell is a cancer cell.

13. The method of claim 12, wherein the cancer cell is a triple negative breast cancer cell.

14. The method of claim 11, wherein the cell is a cell that overexpresses glutathione.

15. A method of delivering combretastatin A-4 to a cell, comprising contacting a cell comprising glutathione with a compound of claim 1, wherein the glutathione cleaves the compound to form combretastatin A-4.

16. The method of claim 15, wherein the cell is a cancer cell.

17. The method of claim 16, wherein the cancer cell is a triple negative breast cancer cell.

18. The method of claim 15, wherein the cell is a cell that overexpresses glutathione.

19. The method of claim 11, wherein the contacting is performed in vivo.

20. The method of claim 11, wherein the contacting is performed in vitro.

21. A method of imaging a glutathione containing cell or population of cells in a subject, comprising:
   administering to the subject a compound of claim 1; and
   detecting fluorescence in the subject, wherein fluorescence indicates a glutathione containing cell or population of cells.

22. The method of claim 21, wherein the glutathione containing cell or population of cells is a cancer cell or cancerous population of cells.

* * * * *

UNITED STATES PATENT AND TRADEMARK OFFICE
CERTIFICATE OF CORRECTION

PATENT NO. : 10,023,551 B2
APPLICATION NO. : 15/573183
DATED : July 17, 2018
INVENTOR(S) : Milton L. Brown et al.

Page 1 of 1

It is certified that error appears in the above-identified patent and that said Letters Patent is hereby corrected as shown below:

In the Claims

At Claim 1, Column 17, Line 43: delete the existing structure and insert the structure:

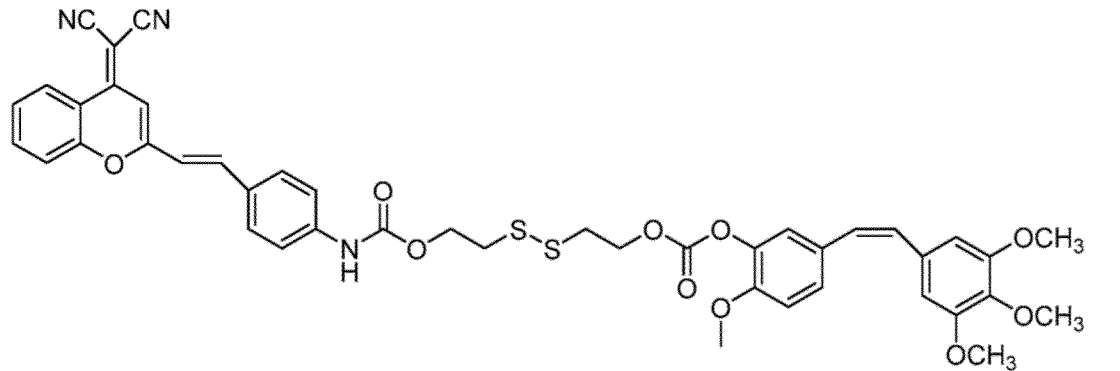

--                                                                                              --

Signed and Sealed this
Fourth Day of September, 2018

Andrei Iancu
*Director of the United States Patent and Trademark Office*